United States Patent
Kamikawa et al.

(10) Patent No.: US 7,122,711 B2
(45) Date of Patent: Oct. 17, 2006

(54) METHOD FOR PRODUCING BIARYL COMPOUND

(75) Inventors: Takashi Kamikawa, Nara (JP); Junji Morimoto, San Marino, CA (US)

(73) Assignee: Sumitomo Chemical Company, Limited, Osaka (JP)

( * ) Notice: Subject to any disclaimer, the term of this patent is extended or adjusted under 35 U.S.C. 154(b) by 689 days.

(21) Appl. No.: 10/294,622

(22) Filed: Nov. 15, 2002

(65) Prior Publication Data

US 2003/0158419 A1    Aug. 21, 2003

(30) Foreign Application Priority Data

Nov. 19, 2001 (JP) .............................. 2001-352796
Nov. 19, 2001 (JP) .............................. 2001-352798

(51) Int. Cl.
*C07C 1/00* (2006.01)

(52) U.S. Cl. ...................................................... 585/469
(58) Field of Classification Search ................. 585/469
See application file for complete search history.

(56) References Cited

FOREIGN PATENT DOCUMENTS

| EP | 0 366 573 A1 | 5/1990 |
|---|---|---|
| FR | 2 804 956 A1 | 8/2001 |
| JP | 2000-229243 A | 8/2000 |
| WO | WO 01/66248 A2 | 9/2001 |

OTHER PUBLICATIONS

T. Kamikawa et al., "Palladium Catalysts for Cross-Coupling of Ortho-Substituted Aryl Triflates with Grignard Reagents", *SYNLETT*, Feb. 1997, pp. 163-164.

K. Tamao et al., "Nickel-Phosphine Complex-Catalyzed Grignard Coupling. I. Cross-Coupling of Alkyl, Aryl, and Alkenyl Gregnard Reagents with Aryl and Alkenyl Halides: General Scope and Limitations", *Bulletin of the Chemical Society of Japan*, vol. 49, No. 7, 1976, pp. 1958-1969.

A. Satake, "Synthesis of Neutral π-Allylpalladium Complexes having Bisnitrogen Ligands and Palladium-Catalyzed Cyclopropanation of Ketene Silyl Acetals with Allylic Acetates", *Yukigosei kagakukyokai-sho*, vol. 58, No. 8, 2000.

V. Böhm et al., "Nickel-Catalyzed Cross-Coupling of Aryl Chlorides with Aryl Grignard Reagents", *Angew. Chem. Int. Ed.*, vol. 39, No. 9, 2000, pp. 1602-1604.

*Primary Examiner*—Thuan Dinh Dang
(74) *Attorney, Agent, or Firm*—Sughrue Mion, PLLC

(57) ABSTRACT

There is disclosed a method for producing a biaryl compound of formula (I):

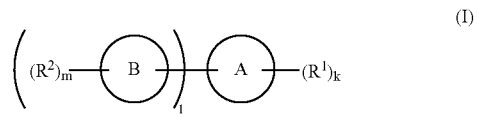

wherein $R^1$ is the same or different and independently denotes a substituted or unsubstituted hydrocarbon group or the like, A and B denote an aromatic hydrocarbon ring having from 6 to 14 carbon atoms or the like, k and m independently denote an integer of from 0 to 5, and l denotes an integer of 1 or 2, which method is characterized by reacting an aromatic compound of formula (II):

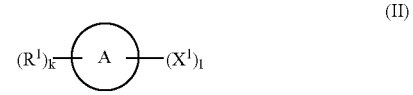

wherein $R^1$, k and l denote the same as defined above, and $X^1$ denotes a leaving group, with a Grignard reagent of formula (III):

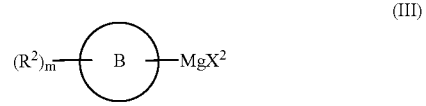

wherein $R^2$, B, and m denote the same as defined above and $X^2$ denotes chlorine or the like, in the presence of a cyclic ether, or an acyclic ether having two or more ether oxygens in the molecule and a nickel catalyst.

19 Claims, No Drawings

METHOD FOR PRODUCING BIARYL COMPOUND

BACKGROUND OF THE INVENTION

Field of the Invention

The present invention relates to a method for producing biaryl compounds.

Biaryl compounds are useful as raw materials or intermediates of medicines, agricultural chemicals, liquid crystal materials and organic EL materials. A cross-coupling reaction of naphthyl or phenyl bromide with a phenyl or naphthyl Grignard reagent by using a nickel complex coordinated with an electron-donating phosphine compound as a ligand was known as a production process of biaryl compounds (Table 7, page 1961, Bulletin of the Chemical Society of Japan, Vol.49(7), 1958–1969(1976)). It is disclosed at lines 3 to 7, left column, at page 1960 of the same Journal that nickel chloride pyridine complex and nickel chloride 2,2'-bipyridyl complex were practically inactive for coupling of butylmagnesium Grignard and chlorobenzene. It is also disclosed in the same Journal and Synlett. 1997, 163 that ortho-disubstituted biaryl compounds were not readily obtainable by such Grignard coupling reaction.

Phosphine compounds are widely used as the ligand of metal complexes, however, there is a problem with phosphorus compounds in that treatments of them after the production are burdensome to the environment. Furthermore, phosphine compounds are readily oxidized and care must be taken to handle them, depending upon the kind of phosphine compound. Moreover, it is, in some cases, difficult to remove and treat resulting phosphorus compounds such as phosphines and phosphine oxides after the reaction.

Although a nitrogen atom is a Group 15 element as phosphorus is and has an ability of coordinating to a metal atom, it is disclosed that the coordination ability of a nitrogen atom is generally inferior to that of a phosphorous atom of phosphine compounds (Yukigoseikagakukyoukaishi, Vol. 58 August 2000, 736–744).

Moreover, a publication of Japanese unexamined patent application, JP-A 2000-229243, discloses a method of coupling an aryl Grignard reagent with a vinyl chloride by using a catalyst containing 1) a compound of a Group 8, 9 or 10 metal of the 4th period of the Periodic Table such as ferric chloride, or [1,3-bis(diphenylphosphino)ethane]nickel chloride(II), 2) at least one compound selected from organometallic compounds of Groups 2 and 3 having no metal hydride structure such as triethylaluminium or triisobutylaluminium, and 3) an electron-donating compound such as triethylamine. This method is not always satisfactory in that phosphine compounds and flammable organometallic compounds of Groups 2 and 3 such as hydrocarbon-substituted aluminum are required.

SUMMARY OF THE INVENTION

According to the present invention, a nickel catalyst comprising a nickel compound and a readily available nitrogen-containing compound effectively catalyzes a Grignard coupling reaction, and a sterically hindered ortho-substituted biaryl compounds can also be readily obtained by the Grignard coupling reaction using the nickel catalyst.

The present invention provides a method for producing a biaryl compound of formula (I):

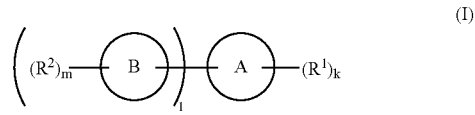

(I)

wherein
R$^1$ is the same or different and independently denotes a substituted or unsubstituted aliphatic hydrocarbon group, a substituted or unsubstituted aryl group, a substituted or unsubstituted alkoxy group, a substituted or unsubstituted aryloxy group, or a fluorine atom, "A" denotes an aromatic hydrocarbon ring having from 6 to 14 carbon atoms or a pyridine ring, "B" denotes an aromatic hydrocarbon ring having from 6 to 14 carbon atoms, k and m independently denote an integer of from 0 to 5, and l denotes an integer of 1 or 2, which method comprises reacting
an aromatic compound of formula (II):

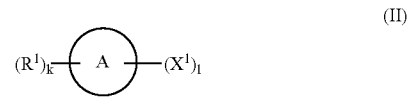

(II)

wherein R$^1$, k and l denote the same as defined above, and X$^1$ denotes a leaving group, with a Grignard reagent of formula (III):

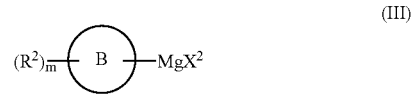

(III)

wherein R$^2$, "B", and m denote the same as defined above, and

X$^2$ denotes a chlorine, bromine or iodine atom, in the presence of a cyclic ether, or an acyclic ether having two or more ether oxygens in the molecule and a nickel catalyst comprising a nickel compound and a nitrogen-containing compound, provided that the nitrogen-containing compound is not 2,2'-bipyridyl.

DETAILED DESCRIPTION OF THE INVENTION

The definitions of R$^1$ and R$^2$ and the substituent groups that maybe present thereon are given first. Unless otherwise defined, the respective terms defined below are the same throughout the present specification.

Examples of the aliphatic hydrocarbon group include, for example,
a straight chain or branched chain, saturated or unsaturated aliphatic hydrocarbon group, typically, having from 1 to 12 carbon atoms, and specific examples thereof include, for example, a methyl group, an ethyl group, a propyl group, an isopropyl group, a butyl group, a sec-butyl group, an isobutyl group, a tert-butyl group, a hexyl group, a heptyl group, an octyl group, a decanyl group, an undecanyl group, a dodecanyl group, a cyclopropyl group, a cyclobutyl group, a cyclopentyl group, a cyclohexyl group, a cycloheptyl group, a vinyl group, a 1-propenyl group, a 2-propenyl group, a 1-methylvinyl group, a 1,3-butadienyl group, a heptenyl group, an octenyl group, an ethynyl group, a 2-propynyl group, a heptynyl group, an octynyl group, arid the like.

Examples of the alkoxyl group include, for example, a straight chain or branched, cyclic or acyclic alkoxyl group, typically having from 1 to 12 carbon atoms, and specific examples thereof include, for example, a methoxy group, an ethoxy group, a propoxy group, an isopropoxy group, a butoxy group, a sec-butoxy group, an iso-butoxy group, a tert-butoxy group, a hexyloxy group, a heptyloxy group, an octyloxy group, a decyloxy group, a dodecyloxy group, a cyclopropyloxy group, a cyclobutyloxy group, a cyclopentyloxy group, a cyclohexyloxy group, a cycloheptyloxy group, etc. Preferred alkoxy groups are methoxy, ethoxy, n-propoxy, I-propoxy, and butoxy groups.

Examples of the aryl group include, for example, an aryl group having from 6 to 14 carbon atoms, and specific examples thereof include, for example, a phenyl group, a naphthyl group, an anthracenyl group, a phenanthryl group, an indenyl group, a fluorenyl group, etc. Preferred are a phenyl group, a naphthyl group, an anthracenyl group, and the like.

Examples of the aryloxy group include, for example, an aryloxy group having from 6 to 14 carbon atoms, and specific examples thereof include, for example, a phenoxy group, a naphthoxy group, an anthracenyloxy group, a phenanthryloxy group, an indenyloxy group, a fluorenyloxy group, etc. Preferred are a phenoxy group, a naphthoxy group, and the like.

The leaving group represented by $X^1$ is not particularly limited as long as it can react with a Grignard reagent, and typical examples thereof include, for example, chlorine, bromine, iodine, a hydrocarbylsulfonate group, a halogen-substituted hydrocarbonsulfonate group or a diazonium group.

Examples of the hydrocarbylsulfonate group include, for example, a methanesulfonate group or a p-toluenesulfonate group.

Examples of the halogen-substituted hydrocarbylsulfonate group include, for example, a trifluoromethanesulfonate group, etc.

Examples of the aromatic hydrocarbon ring having from 6 to 14 carbon atoms represented by "A" include, for example, a benzene ring, a naphthalene ring, an anthracene ring, a phenanthrene ring, an indene ring, a fluorene ring, etc. Preferred are the benzene, naphthalene, and anthracene rings, etc and more preferred is the benzene, or anthracene ring.

When the aromatic rings represented by "A" and "B" are benzene ring, then k+l<7.

Examples of the substituted aliphatic hydrocarbon, aryl, alkoxyl, and aryloxy groups are those groups that are substituted with at least one substituent group selected from a straight chain, branched, or cyclic, saturated or unsaturated aliphatic hydrocarbon group having from 1 to 12 carbon atoms, an aryl group having from 6 to 14 carbon atoms, a straight chain or branched, cyclic alkoxy group having from 1 to 12 carbon atoms, and an aryloxy group having from 6 to 14 carbon atoms, all of which are the same as defined above.

Example of the aromatic compound of formula (II) include, a compound of formula (IV):

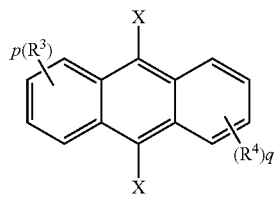

wherein $R^3$ and $R^4$ are the same or different and independently denote an aliphatic hydrocarbon group, an aryl group, an alkoxyl group, an aryloxy group, an aralkyloxy group or a fluorine atom, and p and q independently denote an integer of from 0 to 4, and p+q<5.

The aliphatic hydrocarbon, aryl, alkoxyl, or aryloxy group, or a fluorine atom represented by $R^3$ and $R^4$ has the same meaning as defined for $R^1$ above.

Specific examples of the aryl compound (I) include, for example, substituted phenyl compounds such as bromobenzene, 2-tolyl bromide, 3-tolyl bromide, 4-tolyl bromide, 2-nonylphenyl bromide, 4-cyclohexylphenyl bromide, 2-dodecanylphenyl bromide, 3-decanylphenyl bromide, 4-octylphenyl bromide, 4-dodecanylphenyl bromide, 2-trifluoromethylphenyl bromide, 3-trifluoromethylphenyl bromide, 4-trifluoromethylphenyl bromide, 3-methoxyphenyl bromide, 4-methoxyphenyl bromide, 3-ethoxyphenyl bromide, 4-dodecyloxyphenyl bromide, 2-phenoxyphenyl bromide, 3-phenoxyphenyl bromide, 4-phenoxyphenyl bromide, 3-benzyloxyphenyl bromide, 4-tert-butoxyphenyl bromide, 2,6-dimethylphenyl bromide, 2-phenylphenyl bromide, 4-cyclohexylphenyl bromide, 3-bromobenzotrifluoride, 3-bromo-4-chlorobenzotrifluoride, 1,4-dibromo-2-fluorobenzene, 1,3-dibromobenzene, chlorobenzene, 2-tolyl chloride, 3-tolyl chloride, 4-tolyl chloride, 2-nonylphenyl chloride, 4-cyclohexylphenyl chloride, 2-dodecanylphenyl chloride, 3-decanylphenyl chloride, 4-octylphenyl chloride, 4-dodecanylphenyl chloride, 2-trifluoromethylphenyl chloride, 3-trifluoromethylphenyl chloride, 4-trifluoromethylphenyl chloride, 3-methoxyphenyl chloride, 4-methoxyphenyl chloride, 3-ethoxyphenyl chloride, 4-dodecyloxyphenyl chloride, 2-phenoxyphenyl chloride, 3-phenoxyphenyl chloride, 4-phenoxyphenyl chloride, 3-benzyloxyphenyl chloride, 4-tert-butoxyphenyl chloride, 2,6-dimethylphenyl chloride, 2-phenylphenyl chloride, 4-cyclohexylphenyl chloride, 3-chlorobenzotrifluoride, 3-chloro-4-chlorobenzotrifluoride, 1,4-dichloro-2-fluorobenzene, 1,3-dichlorobenzene, iodobenzene, o-tolyl iodide, 4-tert-butoxyphenyl iodide, 2,6-dimethylphenyl iodide, 2-nonylphenyl iodide, 5-decanylphenyl iodide, 4-octylphenyl iodide, 4-dodecanylphenyl iodide, 1,3-diiodobenzene, 2-chloro-4-fluorotoluene, 3-methoxyphenyl iodide, 1,4-diiodo-2-fluorobenzene, phenyl trifluoromethanesulfonate, 2-methoxyphenyl trifluoromethanesulfonate, 2-chlorophenyl trifluoromethanesulfonate, 2-bromophenyl trifluoromethanesulfonate, 2-iodophenyl trifluoromethanesulfonate, 3-chlorophenyl trifluoromethanesulfonate, 3-bromophenyl trifluoromethanesulfonate, 3-iodophenyl trifluoromethanesulfonate, 4-chlorophenyl trifluoromethanesulfonate, 4-bromophenyl trifluoromethanesulfonate, 4-iodophenyl trifluoromethanesulfonate, 2-tolyl trifluoromethanesulfonate, 3-methoxyphenyl methanesulfonate, phenyl 4-toluenesulfonate, phenyl methanesulfonate, phenyldiazonium tetrafluoroborate salt, etc., substituted naphthyl compounds such as 1-naphthyl bromide, 2-methylnaphthyl bromide, 3-methoxy-2-naphthyl chloride, 1-naphthyl iodide, 2-naphthyltrifluoromethanesulfonate, etc., substituted anthracenyl compounds such as 2-tert-butyl-9,10-dibromoanthracene, 9-bromoanthracene, 9,10-dichloroanthracene, 9-chloroanthracene, 9,10-diiodoanthracene, etc., substituted biphenyls such as 4,4,-dibromobiphenyl, 4,4'-diiodobiphenyl, etc., 9-bromophenanthrene, 2-bromofluorene, 5-bromoindanone, 2,7-dibromobromofluorene, etc and pyridine compound such as 2-bromopyridine, 3-brompyridine, 4-brompyridine or the like.

Specific examples of the Grignard reagent (II) include, for example, phenylmagnesium bromide, 2-tolylmagnesium bromide, 4-methoxyphenylmagnesium bromide, 4-tert-butoxyphenylmagnesium bromide, 2-naphthylmagnesium bromide, 2-methyl-1-naphthylmagnesium bromide, 3,5-di(trifluoromethyl)-phenylmagnesium bromide, 9-anthracenylmagnesium bromide, phenylmagnesium chloride, 4-tert-butoxyphenylmagnesium chloride, 2-tolylmagnesium chloride, 4-methoxyphenylmagnesium chloride, 2-naphthylmagnesium chloride, 2-methyl-1-naphthylmagnesium chloride, 3,5-di(trifluoromethyl)phenylmagnesium chloride, 9-anthracenylmagnesium bromide, phenylmagnesium iodide, 2-tolylmagnesium iodide, 4-methoxyphenylmagnesium iodide, 2-naphthylmagnesium iodide, 2-methyl-1-naphthylmagnesium iodide, 3,5-di (trifluoromethyl) phenylmagnesium iodide, and the like.

The amount of the Grignard reagent (III) that may be suitably used is usually not less than 0.8 mol, preferably not less than 1 mol, and usually not more than 5 moles, preferably not more than 3 moles per mol of one leaving group.

The nickel catalyst suitably used in the present invention comprises, as components, a nickel compound and a nitrogen-containing compound, or is a complex compound in which the nitrogen-containing compound is coordinated to the nickel compound and may be used as the catalyst which was prepared beforehand and isolated as it is, alternatively, nitrogen-containing compound and the nickel compound may be separately added as catalyst components in the present process.

Examples of the nickel compound include, for example, a nickel salt(II) such as nickel halide(II) (e.g. nickel chloride (II), nickel bromide (II), nickel iodide (II)), nickel nitrate (II), nickel acetate (II),), nickel acetylacetonate (II) and a nickel complex(0) (e.g. bis (1,5-cyclooctadiene) nickel (0), nickel carbonyl (0) and the like. The nickel compound may be used in the present reaction as it is commercially available.

Alternatively, it may be used in the present reaction together with a reducing agent. The reducing agent is not particularly limited and specific examples thereof include sodium borohydride, lithium aluminum hydride, sodium hydride, diisobutylaluminum hydride, alkyl Grignard reagents and metallic zinc, etc. The catalyst is typically prepared, by adding the nickel compound, the nitrogen-containing compound, optionally a reducing agent, and a suitable solvent, which does not adversely affect the reaction, that is, that does not react with the reducing agent, may be added, if necessary. However, the order of addition thereof is not particularly limited.

The amount of the reducing agent used is usually 0.1 mol or more, preferably 1 mol or more, and usually 5 moles or less, preferably 3 moles or less per mol of the nickel compound.

The nickel compound may be either dissolved completely or suspended in a reaction mixture.

The nickel compound may be used as it is purchased or alternatively may be made to be bonded to or supported on a carrier, which cannot be dissolved in a reaction solvent used, such as resin, carbon, silica and alumina.

In such a reaction, the amount of the nickel compound that maybe used is usually catalytic, preferably 0.00001 mol or more, and 1 mol or less, more preferably 0.2 mol or less, per mol of the aryl compound (II).

Examples of the nitrogen-containing compound include, for example, an acyclic nitrogen-containing compound and a cyclic nitrogen-containing compound.

Examples of the acyclic nitrogen-containing compound include, for example, an alkylamine having from 1 to 3 nitrogen atoms and from 4 to 20 carbon atoms such as triethylamine, diisopropylethylamine, diisopropylamine, N,N,N',N'-tetramethylethylene-1,2-diamine, N,N,N',N'-tetramethylpropylene-1,3-diamine, N,N,N',N'',N'''-pentamethyldiethylenetriamine, or the like, an alkoxyalkylamine having from 1 to 2 nitrogen atoms, from 5 to 20 carbon atoms and from 1 to 6 oxygen atoms such as tris(2-(2-methoxyethoxy)ethyl)amine, tris(2-methoxyethyl)amine, N,N-diethyl-2-methoxyethylamine or the like, and N-alkylguanidines (e.g. tetramethylguanidine).

Examples of the cyclic nitrogen-containing compound include, for example, a saturated cyclic nitrogen-containing compound, which are formed from the alkylamine or alkoxyamine by bonding the alkyl groups or alkoxyalkyl groups at heir terminals to form an alkylene group or oxaalkylene group, and an unsaturated cyclic nitrogen-containing compound.

Examples of the saturated cyclic nitrogen-containing compound include, for example, piperazine and N,N-dialkylpiperazine (e.g., 1,4-dimethylpiperazine), piperidine and alkylpiperidine (e.g., N-methylpiperidine and 1,2,2,6,6-pentamethylpiperidine), pyrrolidine or N-alkylpyrrolidine (e.g., N-ethylpyrrolidine), N,N',N''-trialkyltriazines (e.g., 1,3,5-trimethyltriazine), N,N',N''-trialkyltriazacycloalkane (e.g. 1,4,7-trimethyltriazacyclononane), morpholine or N-alkylmorpholine (e.g., morpholine and N-methylmorpholine), bicycloalkylamines (e.g., 1,4-diazabicyclo[2.2.2.]octane and quinuclidine, etc).

Examples of the unsaturated cyclic nitrogen-containing compound include, for example, enamine compound (e.g., N-(1-cyclopentenyl)morpholine, diazabicycloalkene (e.g., 1,8-diazabicyclo-[5.4.0]-undec-7-ene and 1,5-diazabicyclo-[4.3.0]-non-b-ene), pyridine, N,N-dialkylaminopyridine, and alkylpyridine (e.g., N,N-dimethylaminopyridine, and methylpyridine), pyrrole and alkylpyrrole including N-alkylpyrrole (e.g., pyrrole, N-isopropylpyrrole and 3-methylpyrrole), imidazole which may be substituted with an alkyl group, which alkyl has preferably from 1 to 15, more preferably 1 to 12 carbon atoms, aryl-alkyl group or an aryl group (e.g., imidazole, N-phenylimidazole, N-methylimidazole, 1,5-dimethylimidazole and N-benzylimidazole), pyrazole which may be substituted with an alkyl or aryl group (e.g., 1-phenyl-1,2-pyrazole, and 1-methyl-1,2-pyrazole), triazole which may be substituted with an alkyl group (e.g., 1,2,4-triazole, and 1-methyl-1,2,3-triazole), tetrazole which may be substituted with an alkyl group (e.g., 1,5-dicyclohexyl-1,2,3,4-tetrazole), benzimidazole which may be substituted with an alkyl group, (e.g., 1-methylbenzimidazole), benzotriazole which may be substituted with an alkyl group (e.g., 1-methyl-1,2,3-benzotriazole), oxazole which may be substituted with an alkyl group (e.g., 3,5-dimethyloxazole), benzoxazole compound (e.g., benzoxazole), benzothiazole compound (e.g., benzothiazole), carbazole and N-alkylcarbazole, (e.g., carbazole and N-ethylcarbazole), quinoline compound (e.g., quinoline), phthalazine compound (e.g., phthalazine), quinazoline compound (e.g., quinazoline), pyrimidine which may be substituted with an alkyl group (e.g., 4-ethylpyrimidine), cyclic urea compound (e.g. N,N-dimethylimidazolidone and N,N-dimethyl-propyleneurea) and the like.

Preferred acyclic nitrogen-containing compounds and cyclic nitrogen-containing compounds are those having tertiary nitrogen atom or atoms, more preferred are the imidazoles, alkylamines, alkoxyalkylamines N,N-dialkylaminopyridines and diazabicycloalkenes as specified above.

Specific examples of the preferred acyclic nitrogen-containing compounds and cyclic nitrogen-containing compounds having tertiary nitrogen atom or atoms include, for example, triethylamine, diisopropylethylamine, N,N,N',N'-tetramethylethylene-1,2-diamine, N,N,N',N'-tetramethylpropylene-1,3-diamine, N,N,N',N'',N''-pentamethyldiethylenetriamine, tris(2-(2-methoxyethoxy)ethyl)amine, tris(2-methoxyethyl)amine, N,N-diethyl-2-methoxyethylamine, tetramethylguanidine, 1,4-dimethylpiperazine, N-methylpiperidine, 1,2,2,6,6-pentamethylpiperidine, N-ethylpyrrolidine, 1,3,5-trimethyltriazine, 1,4,7-trimethyltriazacyclononane, N-methylmorpholine, 1,4-diazabicyclo[2,2,2.]octane, quinuclidine, N-(1-cyclopentenyl)morpholine, 1,8-diazabicyclo-[5.4.0]-undec-7-ene, 1,5-diazabicyclo-[4.3.0]-non-5-ene, N,N-dimethylaminopyridine, N-isopropylpyrrole, N-phenylimidazole, N-methylimidazole, 1,5-dimethylimidazole, N-benzylimidazole, 1-phenyl-1,2-pyrazole, 1-methyl-1,2-pyrazole, 1-methyl-1,2,3-triazole, 1,5-dicyclohexyl-1,2,3,4-tetrazole, 1-methylbenzimidazole, 1-methyl-1,2,3-benzotriazole, 2,4,5-trimethyloxazole, benzoxazole, benzothiazole, N-ethylcarbazole, quinoline, phthalazine, quinazoline, 4-ethylpyrimidine, N,N-dimethylimidazolidone, N,N-dimethylpropyleneurea and the like.

Alternatively, preferred nitrogen compounds are those of which conjugated acids have pKa of 1 or more, preferably 3 or more, more preferably 5.5 or more, yet more preferably 6 or more. The pKa of the conjugated acid referred to herein can be calculated using commercially available software for pKa calculation, ACD/pKa (version 1.0) available from L.A. SYSTEMS Inc., and an updated version may be relied on, if appropriate) As for the software, a web-site, http://acdlabs.com. can be referred to. ACD/pKa is a program that calculates acid-base ionization constants (pKa values) under 25° C. and zero ionic strength in aqueous solutions for a given organic structure. Each calculation is provided with both its ±95% confidence limits and a detailed report of how it has been carried out, including Hammett-type equation(s), substituent constants, and literature references where available.

The amount of the nitrogen-containing compound used based on the metal of the nickel compound is usually catalytic, preferably not less than 0.05 mol, more preferably not less than 0.5 mol, and is preferably not more than 100 moles, more preferably not more than 10 moles per gram atom of the nickel atom. When the nitrogen-containing compound is in a liquid format a reaction temperature, an excess amount of the nitrogen-containing compound may be used as a solvent. In such a case, the nitrogen-containing compound may be use, for example, in an amount of from 1 ml to 20 ml based on 1 mmol of the aryl compound.

A single nitrogen-containing compound may be used or, alternatively, two or more nitrogen-containing compounds may be used in combination. Such a nitrogen-containing compound carried on a suitable support may be used, and examples of the support include a resin, which does not be dissolved in a reaction solvent.

Examples of the cyclic ether include, for example, 5- to 8-membered monocyclic ethers having from 1 to 3 ether oxygen atoms, and specific examples thereof include, for example, a tetrahydrofuran, dioxane, etc.

Examples of the acyclic ether having two or more ether oxygen atoms in the molecule include acyclic ethers having from 4 to 8 carbon atoms, and preferred is the acyclic ethers having from 2 to 4 ether oxygen atom.

Specific examples thereof include, for example, ethylene glycol dimethyl ether, diethylene glycol dimethyl ether, triethylene glycol dimethyl ether, tetramethylene ether dimethyl ether, ethylene glycol diethyl ether, diethylene glycol diethyl ethers triethylene glycol diethyl ether, and tetramethylene ether diethyl ether.

The cyclic or acyclic ether having two or more ether oxygen atoms in the molecule may be used in a catalytic amount or may be used as the ether solvent as described below.

The reaction of the present invention is usually carried out in an organic solvent. Examples of the solvent include ether solvents such as diethyl ether, diisopropyl ether, diethylene glycol dimethyl ether, 1,4-dioxane and tetrahydrofuran, aromatic hydrocarbons such as benzene, toluene and xylene, aliphatic hydrocarbons such as hexane and heptane, etc. Such organic solvents are used singly or in combination of two or more of them. The amount thereof is usually not less than 1 part and not more than 200 parts, preferably not less than 5 parts and not more than 100 parts by weight per weight of the aryl compound. Among those solvents, ether solvents are preferred. 1,4-Dioxane and glymes are more preferably used for the production of non-ortho-substituted aromatic compound.

In the production method of the present invention, one may add the aryl compound (I), Grignard reagent (II), the nickel compound, and the nitrogen-containing compound in an optional order by using a suitable solvent, if necessary. In order to allow the reaction to proceed, one may mix the nickel compound, which was previously dried, in a solvent under an atmosphere of an inert gas such as a nitrogen gas, an argon gas, etc., and a nitrogen-containing compound and mix the aryl compound (II) and the Grignard reagent (III) in an optional order. One also may feed a mixture prepared from the nickel compound and the nitrogen-containing compound to a system prepared by adding the aryl compound (II), the Grignard reagent (III), and, if necessary, a suitable solvent in an optional order under an atmosphere of an inert gas such as a nitrogen gas, an argon gas, etc. The above reaction mixtures may be dissolved completely in the solvents. Alternatively, part of a mixture may be present as a solid in a solvent instead of being dissolved.

When a reducing agent is used, those compounds may be fed in an optional order. For example, one may add the nickel compound, which was previously dried, in a solvent under an atmosphere of an inert gas such as a nitrogen gas, an argon gas, etc., and a nitrogen-containing compound in an optional order, and then add a reducing agent, and also add the aryl compound (II) and the Grignard reagent (III) in an optional order. One also may add the nickel compound, which was previously dried, in a solvent under an atmosphere of an inert gas such as a nitrogen gas, an argon gas, etc., the nitrogen-containing compound and the aryl compound in an arbitrary order, and then add a reducing agent, and add the Grignard reagent in an optional order. Furthermore, a mixture prepared from the nickel compound, the Grignard reagent (II) and the reducing agent, for example, may be added to a system prepared by adding an aryl compound, the Grignard reagent (II) in an optional order, and if necessary, a suitable solvent under an atmosphere of an inert gas such as a nitrogen gas, an argon gas, etc. The above reaction mixtures may be dissolved completely in the solvents. Alternatively, a part of the mixture may be present as a solid in a solvent instead of being dissolved.

The reaction temperature is usually not lower than −40° C., preferably not lower than −20° C., and is usually not higher than 200° C., and, if the boiling point of the organic solvent is lower than 200° C. and not higher than the boiling point.

In such a way, biaryl compound is formed. Subsequently, the biaryl compound (I) may be separated in such a way that an acid is added so as to inactivate the remaining Grignard reagent and then, for example, separation by extraction is conducted. After that, the product may be purified by distillation, if necessary. Alternatively, an ortho-substituted biaryl compound, which is typically produced as crystals, can be separated after crystallization. The ortho-substituted aromatic compound may also separated as crystals by mixing the resulting reaction mixture with an insufficient solvent so as to precipitate the ortho-substituted biaryl compound. In still another way, the resulting reaction mixture is concentrated so that an ortho-substutyted biaryl compound is precipitated. The crystals can be separated readily, for example, by filtration. Furthermore, crystals of a substituted aromatic compound can be obtained by removing a solvent from a reaction mixture by distillation, followed by further removal of a solvent by distillation. It can also be separated by conventional chromatography or distillation. These post-treatment can readily separate nickel compounds and nitrogen-containing compounds contained in a reaction mixture. The ortho-substituted biaryl compound separated may be purified further by chromatography, distillation, recrystallization, or the like.

Specific examples of the biaryl compound of formula (I) include, for example, 2-methyl-1,1'-biphenyl, 2-hexyl-1,1'-biphenyl, 2-isopropyl-1,1'-biphenyl, 2-cyclohexyl-1,1'-biphenyl, 2-dodecanyl-1,1'-biphenyl, 3-cyclohexyl-1,1'-biphenyl, 4-dodecanyl-1,1'-biphenyl, 4-dodecanyl-1,1':4',1"-terphenyl, ,4-dodecanyl-1,1':2',1"-terphenyl, 2-methyl-2'-ethyl-1,1'-biphenyl, 2,5-dimethyl-1,1'-biphenyl, 2,2'-dimethyl-1,1'-biphenyl, 4'-tert-butoxy-2-methyl-1,1'-biphenyl, 2,5,2'-trimethyl-1,1'-biphenyl, 1-phenylnaphthalene, 2-methyl-1-(2'-methylphenyl)-naphthalene, 9-phenylanthracene, 9-(2-naphthyl)anthracene, 9,10-diphenylanthracene, 9,10-di(3,5-dimethoxyphenyl)anthracene, 2-tert-butyl-9,10-diphenylanthracene, 9,10-di(2-naphthyl)anthracene, 1,4-dimethoxy-5,8-dimethyl-9,10-diphenylanthracene, 2,2'-(1,1'-biphenyl)-4,4'-diylbis(9,10-diphenylanthracene), 9,9',10,10'-tetraphenyl-1,1'-bianthracene, 1,2,3,4-tetramethyl-9,10-diphenylanthracene, 1-(methoxymethoxy)-9,10-diphenylanthracene, 2-[(3,3-dimethylcyclopentyl)methyl]-9,10-diphenylanthracene, 1,4,5-trifluoro-9,10-diphenylanthracene, 2,3,6,7-tetramethoxy-9,10-diphenylanthracene, 2,4-dimethoxy-1-methyl-9,10-diphenylanthracene, 2-vinyl-9,10-diphenylanthracene, 10,10'-diphenyl-9,9'-bianthracene, etc.

Preferred compounds are those compounds having the ring "A" representing an aromatic hydrocarbon ring and at least one ortho-hydrogen atom on the four ortho-positions of the carbon atoms that are connected by the biaryl single bond formed by the Grignard coupling reaction. Such compound can typically be obtained by reacting the aromatic compound of formula (II) or the Grignard compound of formula (III) wherein at least one ortho-carbon atom of the aromatic compound of formula (II) or the Grignard compound of formula (III) is substituted with a hydrogen atom, wherein the ortho-carbon atom is defined in relation to the carbon atom bonded with $X^1$ group or $MgX^2$ group. Thus, not only mono-ortho-substituted biaryl compound but also di-ortho-substituted, and tri-ortho-substituted biaryl compounds as described above can be readily prepared by the presently claimed process.

Specific examples of the preferred compound include, for example, 2-methyl-1-(2'-methylphenyl)-naphthalene, 9-phenylanthracene, 9-(2-naphthyl)anthracene, 9,10-diphenylanthracene, 9,10-di(3,5-dimethoxyphenyl)anthracene, 2-t-butyl-9,10-diphenylanthracene, 9,10-di(2-naphthyl)anthracene, 1,4-dimethoxy-5,8-dimethyl-9,10-diphenylanthracene, 2,2'-(1,1'-biphenyl)-4,4'-diylbis(9,10-diphenylanthracene), 9,9',10,10'-tetraphenyl-1,1'bianthracene, 1,2,3,4-tetramethyl-9,10-diphenylanthracene, 1-(methoxymethoxy)-9,10-diphenylanthracene, 2-[(3,3-dimethylcyclopentyl)methyl]-9,10-diphenylanthracene, 1,4,5-trifluoro-9,10-diphenylanthracene, 2,3,6,7-tetramethoxy-9,10-diphenylanthracene, 2,4-dimethoxy-1-methyl-9,10-diphenylanthracene, 2-viny-9,10-diphenylanthracene, 10,10'-diphenyl-9,9'-bianthracene, and the like.

According to the present invention, substituted aromatic compounds can be produced.

EXAMPLES

The present invention is described in detail below by way of examples, but it is not to be construed to limit the invention thereto. The contents shown below are values obtained through analysis of a reaction mixture by gas chromatography, followed by area ratios of individual gas chromatogram areas of the desired substituted aromatic compound, the unreacted aryl compound and impurities derived from the aryl compound to the total gas chromatogram areas of these components.

Example 1

Under a nitrogen atmosphere, 3.2 mg (0.025 mmol) of dry $NiCl_2$ and 4.1 mg (0.05 mmol) of N-methylimidazole were added to 0.9 ml of diethylene glycol dimethyl ether and were stirred at 25° C. for 10 minutes. Subsequently, 67.2 mg (0.5 mmol) of m-bromotoluene was added at that temperature and reduced-pressure nitrogen replacement was conducted. To the resulting reaction mixture, 0.20 ml (0.6 mmol) of a 3 mol/l solution of phenylmagnesium bromide in diethyl ether was added and stirred at 25° C. for 4 hours.

Decomposition of an excess Grignard reagent with a 10% hydrochloric acid was followed by extraction with ethyl acetate. The organic layer was washed with water. The organic layer contained 3-methylbiphenyl, which is the desired compound, in a content of 70.1%.

Example 2

Under a nitrogen atmosphere, 3.2 mg (0.025 mmol) of dry $NiCl_2$ and 4.1 mg (0.05 mmol) of N-methylimidazole were added to 0.5 ml of diethylene glycol dimethyl ether and were stirred at 25° C. for 10 minutes. Subsequently, 67.2 mg (0.5 mmol) of m-bromotoluene was added at that temperature and reduced-pressure nitrogen replacement was conducted. To the resulting reaction mixture, 0.40 ml (0.6 mmol) of a 1.5 mol/l solution of phenylmagnesium bromide in diethyl ether was added, heated to 65° C., and stirred at this temperature for 4 hours.

Decomposition of an excess Grignard reagent with a 10% hydrochloric acid was followed by extraction with ethyl acetate. The organic layer was washed with water. The organic layer contained 3-methylbiphenyl, which is the desired compound, in a content of 79.9%.

Example 3

Under a nitrogen atmosphere, 3.2 mg (0.025 mmol) of dry $NiCl_2$ and 4.1 mg (0.05 mmol) of N-methylimidazole were added to 0.7 ml of diethylene glycol dimethyl ether and were stirred at 25° C. for 10 minutes. Subsequently, 0.067 ml (0.06 mmol) of a 1 mol/l solution of methylmagnesium bromide in tetrahydrofuran was added and stirred at that temperature for 10 minutes. Moreover, 67.2 mg (0.5 mmol) of m-bromotoluene was added at that temperature and reduced-pressure nitrogen replacement was conducted. To the resulting reaction mixture, 0.40 ml (0.6 mmol) of a 1.5 mol/l solution of phenylmagnesium bromide in diethyl ether was added, heated to 65° C., and stirred at this temperature for 4 hours.

Decomposition of an excess Grignard reagent with a 10% hydrochloric acid was followed by extraction with ethyl acetate. The organic layer was washed with water. The organic layer contained 3-methylbiphenyl, which is the desired compound, in a content of 77.3%.

Example 4

Under a nitrogen atmosphere, 3.2 mg (0.025 mmol) of dry $NiCl_2$ and 5.1 mg (0.05 mmol) of triethylamine were added to 0.7 ml of diethylene glycol dimethyl ether and were stirred at 25° C. for 10 minutes. Subsequently, 67.2 mg (0.5 mmol) of o-bromotoluene was added at that temperature and reduced-pressure nitrogen replacement was conducted. To the resulting reaction mixture, 0.40 ml (0.6 mmol) of a 1.5 mol/l solution of phenylmagnesium bromide in diethyl ether was added and stirred at this temperature for 4 hours.

Decomposition of an excess Grignard reagent with a 10% hydrochloric acid was followed by extraction with ethyl acetate. The organic layer was washed with water. The organic layer contained 2-methylbiphenyl, which is the desired compound, in a content of 68.2%.

Example 5

Under a nitrogen atmosphere, 3.2 mg (0.025 mmol) of dry $NiCl_2$ and 5.1 mg (0.05 mmol) of triethylamine were added to 0.5 ml of tetrahydrofuran and were stirred at 25° C. for 10 minutes. Subsequently, 0.067 ml (0.06 mmol) of a 1 mol/l solution of methylmagnesium bromide in tetrahydrofuran was added and stirred at that temperature for 10 minutes. Moreover, 67.2 mg (0.5 mmol) of o-bromotoluene was added at that temperature and reduced-pressure nitrogen replacement was conducted. To the resulting reaction mixture, 0.40 ml (0.6 mmol) of a 1.5 mol/l solution of phenylmagnesium bromide in di ethyl ether was added, heated to 65° C., and stirred at this temperature for 4 hours.

Decomposition of an excess Grignard reagent with a 10% hydrochloric acid was followed by extraction with ethyl acetate. The organic layer was washed with water. The organic layer contained 2-methylbiphenyl, which is the desired compound, in a content of 60.4%.

Example 6

Under a nitrogen atmosphere, 3.2 mg (0.025 mmol) of dry $NiCl_2$ and 4.1 mg (0.05 mmol) of N-methylimidazole were added to 0.5 ml of THF and were stirred at 25° C. for 10 minutes. Subsequently, 67.2 mg (0.5 mmol) of m-bromotoluene was added at that temperature and reduced-pressure nitrogen replacement was conducted. To the resulting reaction mixture, 0.67 ml (0.6 mmol) of a 1 mol/l solution of phenylmagnesium bromide in tetrahydrofuran was added, heated to 65° C., and stirred at this temperature for 4 hours.

Decomposition of an excess Grignard reagent with a 10% hydrochloric acid was followed by extraction with ethyl acetate. The organic layer was washed with water. The organic layer contained 3-methylbiphenyl, which is the desired compound, in a content of 42.3%.

Comparative Example 1

Under a nitrogen atmosphere, 3.2 mg (0.025 mmol) of dry $NiCl_2$ and 4.1 mg (0.05 mmol) of N-methylimidazole were added to 0.9 ml of diethyl ether and were stirred at 25° C. for 10 minutes. Subsequently, 67.2 mg (0.5 mmol) of m-bromotoluene was added at that temperature and reduced-pressure nitrogen replacement was conducted. To the resulting reaction mixture, 0.20 ml (0.6 mmol) of a 3 mol/l solution of phenylmagnesium bromide in diethyl ether was added and stirred at 25° C. for 4 hours.

Decomposition of an excess Grignard reagent with a 10% hydrochloric acid was followed by extraction with ethyl acetate. The organic layer was washed with water. The organic layer contained 3-methylbiphenyl, which is the desired compound, in a content of 17.8%.

Comparative Example 2

Under a nitrogen atmosphere, 4.1 mg (0.025 mmol) of dry $FeCl_3$ and 5.1 mg (0.05 mmol) of triethylamine were added to 0.5 ml of THF and were stirred at 25° C. for 10 minutes. Subsequently, 67.2 mg (0.5 mmol) of o-bromotoluene was added at that temperature and reduced-pressure nitrogen replacement was conducted. To the resulting reaction mixture, 0.60 ml (0.6 mmol) of a 1 mol/l solution of phenylmagnesium bromide in tetrahydrofuran was added, heated to 65° C. and stirred at this temperature for 4 hours.

Decomposition of an excess Grignard reagent with a 10% hydrochloric acid was followed by extraction with ethyl acetate. The organic layer was washed with water. The organic layer contained 2-methylbiphenyl, which is the desired compound, in a content of 1.1%.

Example 7

Under a nitrogen atmosphere, 3.2 mg (0.025 mmol) of dry $NiCl_2$ and 4.1 mg (0.05 mmol) of N-methylimidazole were added to 0.5 ml of 1,4-dioxane and were stirred at 25° C. for 10 minutes. Subsequently, 63.3 mg (0.5 mmol) of o-chlorotoluene was added at that temperature and reduced-pressure nitrogen replacement was conducted. To the reaction mixture, 0.067 ml (0.063 mmol) of a 0.93 mol/l solution of methylmagnesium bromide in tetrahydrofuran was added and stirred at 25° C. for another 10 minutes. To the resulting reaction mixture, 0.60 ml (0.6 mmol) of a 1 mol/l solution of phenylmagnesium bromide in tetrahydrofuran was added, heated to 65° C. and stirred at this temperature for 4 hours.

Decomposition of an excess Grignard reagent with a 10% hydrochloric acid was followed by extraction with ethyl acetate. The organic layer was washed with water. The organic layer contained 2-methylbiphenyl, which is the desired compound, in a content of 77.1%.

Example 8

Operations were conducted in the same manner as Example 7 except for using 1,8-diazabicyclo-[5.4.0]-undec-7-ene (0.05 mmol) in place of N-methylimidazole.

Example 9

Operations were conducted in the same manner as Example 7 except for using quinuclidine (0.05 mmol) in place of N-methylimidazole.

Example 10

Operations were conducted in the same manner as Example 7 except for using 2-chloropyridine (0.05 mmol) instead of o-chlorotoluene.

Example 11

Operations were conducted in the same manner as Example 7 except for using tris(2-(2-methoxyethy)ethyl) amine (0.05 mmol), m-chlorotoluene (0.05 mmol) and tetrahydrofuran in place of N-methylimidazole, o-chlorotoluene and 1,4-dioxane, respectively.

Example 12

Under a nitrogen atmosphere, 3.2 mg (0.025 mmol) of dry $NiCl_2$ and 4.1 mg (0.05 mmol) of N-methylimidazole were added to 0.5 ml of diethylene glycol dimethyl ether and were stirred at 25° C. for 10 minutes. Subsequently, 93.5 my (0.5 mmol) of p-bromoanisole was added at that temperature and reduced-pressure nitrogen replacement was conducted. To the reaction mixture, 0.067 ml (0.063 mmol) of a 0.93 mol/l solution of methylmagnesium bromide in tetrahydrofuran was added and stirred at 25° C. for another 10 minutes. To the resulting reaction mixture, 0.60 ml (0.6 mmol) of a 1 mol/l solution of phenylmagnesium bromide in tetrahydrofuran was added, heated to 65° C., and stirred at this temperature for 4 hours.

Decomposition of an excess Grignard reagent with a 10% hydrochloric acid was followed by extraction with ethyl acetate. The organic layer was washed with water. The organic layer contained 4-methylbiphenyl, which is the desired compound, in a content of 68.8%.

Example 13

Operations were conducted in the same manner as Example 12 except for using p-trifluoromethylbromobenzene (0.5 mmol) in place of p-bromoanisole.

Example 14

Operations were conducted in the same manner as Example 12 except for using o-bromotoluene (0.5 mmol) and triethylene glycol dimethyl ether in place of p-bromoanisole and diethylene glycol dimethyl ether, respectively.

Example 15

Operations were conducted in the same manner as Example 12 except for using triethylamine (0.05 mmol), o-bromotoluene (0.5 mmol) and triethylene glycol dimethyl ether in place of N.-methylimidazole, p-bromoanisole and diethylene glycol dimethyl ether, respectively.

The results of Examples 7–15 are summarized in Table 1.

TABLE 1

| Example | Aromatic compound (II) | Solvent | Nitrogen-containing compound | Content of substituted biaryl compound |
| --- | --- | --- | --- | --- |
| Example 7 | o-Chlorotoluene | 1,4-Dioxane | N-methylimidazole | 77.1% |
| Example 8 | o-Chlorotoluene | 1,4-Dioxane | 1,8-Diazabicyclo-[5.4.0]-undec-7-ene | 78.2% |
| Example 9 | o-Chlorotoluene | 1,4-Dioxane | Quinuclidien | 70.2% |
| Example 10 | 2-Chloropyridine | 1,4-Dioxane | N-Methylimidazole | 84.5% |
| Example 11 | m-Chlorotoluene | Tetrahydrofuran | Tris (2-(2-methoxyethoxy)-ethyl) amine | 82.9% |
| Example 12 | p-Bromoanisole | Diethylene glycol dimethyl ether | N-Methylimidazole | 68.8% |
| Example 13 | p-Trifluoromethyl bromobenzene | Diethylene glycol dimethyl ether | N-Methylimidazole | 82.8% |
| Example 14 | o-Bromotoluene | Triethylene glycol dimethyl ether | N-Methylimidazole | 72.4% |
| Example 15 | o-Bromotoluene | Triethylene glycol dimethyl ether | Triethylamine | 76.5% |

Example 16

Under a nitrogen atmosphere, 35.7 mg (0.15 mmol) of dry NiCl$_2$ and 30.3 mg (0.3 mmol) of triethylamine were added to 10.1 ml of diethylene glycol dimethyl ether and were stirred at 20° C. for 10 minutes. Subsequently, 10.1 g (30.0 mmol) of 9,10-dibromoanthracene was added at that temperature and reduced-pressure nitrogen replacement was conducted. To the reaction mixture, 0.40 ml (0.38 mmol) of a 0.93 mol/l solution of methylmagnesium bromide in tetrahydrofuran was added and stirred at 25° C. for another 10 minutes. To the resulting reaction mixture, 69 ml (69 mmol) of a 1 mol/l solution of phenylmagnesium bromide in tetrahydrofuran was added dropwise over 50 minutes. The temperature of the reaction mixture after the addition was 24° C. This mixture was heated to 65° C. and then stirred at this temperature for 4 hours.

Decomposition of an excess Grignard reagent with a 10% hydrochloric acid was followed by extraction with ethyl acetate. The organic layer was washed with water. The organic layer contained 9,10-diphenylanthracene, which is the desired compound, in a content of 96.25%.

Example 17

Operations were conducted in the same manner as Example 16 except for using tetrahydrofuran in place of diethylene glycol dimethyl ether.

Example 18

Operations were conducted in the same manner as Example 16 except for using toluene in place of diethylene glycol dimethyl ether.

Example 19

Operations were conducted in the same manner as Example 16 except for using 7.1 mg (0.03 mmol) of NiCl$_2$, 6.1 mg (0.006 mmol) of triethylamine, and 0.08 ml (0.075 mmol) of a 0.93 mol/l solution of methylmagnesium in tetrahydrofuran in place of 35.7 mg (0.15 mmol) of NiCl$_2$, 30.3 mg (0.3 mmol) of triethylamine, and 0.40 ml (0.38 mmol) of a 0.93 mol/l solution of methylmagnesium bromide in tetrahydrofuran, respectively.

The results of Examples 16–19 are summarized in Table 2.

TABLE 2

| Example | Solvent | Amount of NiCl$_2$ | Content of substituted aromatic compound |
|---|---|---|---|
| Example 16 | Diethylene glycol dimethyl ether | 0.15 mmol (0.5 mol % based on unsaturated organic compound) | 96.0% |
| Example 17 | Tetrahydrofuran | 0.15 mmol (0.5 mol % based on unsaturated organic compound) | 90.5% |
| Example 18 | Toluene | 0.15 mmol (0.5 mol % based on unsaturated organic compound) | 90.3% |
| Example 19 | Diethylene glycol dimethyl ether | 0.03 mmol (0.1 mol % based on unsaturated organic compound) | 93.9% |

Example 20

Under a nitrogen atmosphere, 3.2 mg (0.025 mmol) of dry NiCl$_2$ and 4.1 mg (0.05 mmol) of N-methylimidazole were added to 0.5 ml of THF and were stirred at 25° C. for 10 minutes. Subsequently, 67.2 mg (0.5 mmol) of o-bromotoluene was added at that temperature. To the reaction mixture, 0.60 ml (0.6 mmol) of a 1 mol/l solution of 2,6-dimethylphenylmagnesium bromide in tetrahydrofuran was added, heated to 65° C., and stirred at this temperature for 4 hours.

Decomposition of an excess Grignard reagent with a 10% hydrochloric acid was followed by extraction with ethyl acetate. The organic layer was washed with water. The organic layer contained 2,6,2'-trimethylbiphenyl, which is the desired compound, in a content of 81.7%.

Example 21

Under a nitrogen atmosphere, 3.2 mg (0.025 mmol) of dry NiCl$_2$ and 4.1 mg (0.05 mmol) of N-methylimidazole were added to 0.5 ml of THF and were stirred at 25° C. for 10 minutes. Subsequently, 67.2 mg (0.5 mmol) of o-bromotoluene was added at that temperature. To the reaction mixture, 0.067 ml (0.06 mmol) of a 1 mol/l solution of methylmagnesium bromide in tetrahydrofuran was added, and then stirred and mixed for 10 minutes. Subsequently, 0.6 ml (0.6 mmol) of a 1 mol/l solution of 2,6-dimethylphenylmagnesium bromide in tetrahydrofuran was added, heated to 65° C., and stirred at this temperature for 4 hours.

Decomposition of an excess Grignard reagent with a 10% hydrochloric acid was followed by extraction with ethyl acetate. The organic layer was washed with water. The organic layer contained 2,6,2'-trimethylbiphenyl, which is the desired compound, in a content of 92.8%.

Example 22

Operations were conducted in the same manner as Example 21 except for using 0.05 mmol of N,N,N',N'',N''-pentamethyldiethylenetriamine in place of N-methylimidazole in Example 21.

Example 23

Operations were conducted in the same manner as Example 21 except for using 0.05 mmol of tris(2-methoxyethyl-2'-ethoxy)amine in place of N-methylimidazole in Example 21.

Example 24

Operations were conducted in the same manner as Example 21 except for using 0.025 mmol of PdCl$_2$ and 0.05 mmol of triethylamine in place of NiCl$_2$ and N-methylimidazole in Example 21, respectively. The result is shown in Table 3.

Example 25

Synthesis of 2-methyl-1-o-tolyl-naphthalene was conducted in the same manner as Example 20 except for using 0.5 mmol of 2-methyl-1-bromonaphthalene, 0.60 ml (0.6 mmol) of a 1 mol/l solution of o-tolylmagnesium chloride in tetrahydrofuran, and 0.05 mmol of triethylamine in place of o-bromotoluene, 0.60 ml (0.6 mmol) of a 1 mol/l solution of 2,6-dimethylphenylmagnesium bromide in tetrahydrofuran, and N-methylimidazole in Example 20, respectively The result is shown in Table 3.

Example 26

Synthesis of 2-methyl-1-o-tolyl-naphthalene was conducted in the same manner as Example 21 except for using 0.5 mmol of 2-methyl-l-bromonaphthalene, 0.60 ml (0.6 mmol) of a 1 mol/l solution of o-tolylmagnesium chloride in tetrahydrofuran, and 0.05 mmol of 1,8-diazabicyclo-[5.4.0]-undec-7-ene in place of o-bromotoluene, 0.60 ml (0.6 mmol) of a 1 mol/l solution of 2,6-dimethylphenylmagnesium bromide in tetrahydrofuran, and N-methylimidazole in Example 21, respectively The result is shown in Table 3.

Example 27

Synthesis of 2,2',3'-trimethylbiphenyl was conducted in the same manner as Example 21 except for using 0.5 mmol of 3-bromo-o-xylene, 0.60 ml (0.6 mmol) of a 1 mol/l solution of o-tolylmagnesium chloride in tetrahydrofuran, and 0.05 mmol of 4-(N,N-dimethylamino)pyridine in place of o-bromotoluene, 0.60 ml (0.6 mmol) of a 1 mol/l solution of 2,6-dimethylphenylmagnesium bromide in tetrahydrofuran, and N-methylimidazole in Example 21, respectively The result is shown in Table 3.

Example 28

Synthesis of 9-(2-naphthyl)anthracene was conducted in the same manner as Example 21 except for using 0.5 mmol of 9-bromoanthracene, 0.43 ml (0.6 mmol) of a 1.4 mol/l solution of 2-naphthylmagnesium bromide in tetrahydrofuran, and 0.05 mmol of triethylamine in place of o-bromotoluene, 0.60 ml (0.6 mol/i solution of 2,6-dimethylphenylmagnesium bromide in tetrahydrofuran, and N-methylimidazole in Example 21, respectively The result is shown in Table 3.

Example 29

Synthesis of 9-phenylanthracene was conducted in the same manner as Example 21 except for using 0.5 mmol of 9-chloroanthracene and 0.60 ml (0.6 mmol) of a 1 mol/l solution of phenylmagnesium bromide in tetrahydrofuran in place of o-bromotoluene and 0.60 ml (0.6 mmol) of a 1 mol/l solution of 2,6-dimethylphenylmagnesium bromide in tetrahydrofuran in Example 21, respectively The result is shown in Table 3.

Example 30

Synthesis of 9, 10-diphenylanthracene was conducted in the same manner as Example 21 except for using 0.5 mmol of 9,10-dibromoanthracene, 1.2 ml (1.2 mmol) of a 1 mol/l solution of phenylmagnesium bromide in tetrahydrofuran, and 0.05 mmol of triethylamine in place of o-bromotoluene, 0.60 ml (0.6 mmol) of a 1 mol/l solution of 2,6-dimethylphenylmagnesium bromide in tetrahydrofuran, and N-methylimidazole in Example 21, respectively The result is shown in Table 3.

Example 31

Synthesis of 2-methylbiphenyl was conducted in the same manner as Example 29 except for using 63.3 mg (0.5 mmol) of o-chlorotoluene and 7.6 mg (0.05 mmol) of 1,8-diazabicyclo-[5.4.0]-undec-7-ene in place of 9-chloroanthracene and N-methylimidazole in Example 29, respectively The result is shown in Table 3.

Example 32

Synthesis of 3-methylbiphenyl was conducted in the same manner as Example 30 except for using 17 mg (0.5 mmol) of m-bromotoluene in place of 9-chloroanthracene in Example 30. The result is shown in Table 3.

Comparative Example 3

Operations were conducted in the same manner as Example 21 except for using 0.05 mmol of 2,2'-bipyridyl in place of N-methylimidazole in Example 21. The result is shown in Table 3.

Comparative Example 4

Operations were conducted in the same manner as Example 32 except for using 0.05 mmol of 2,2'-bipyridyl in place of triethylamine in Example 32. The result is shown in Table 3.

Comparative Example 5

Operations were conducted in the same manner as Example 33 except for using 0.05 mmol of 2,2'-bipyridyl in place of triethylamine in Example 33. The result is shown in Table 3.

Comparative Example 6

Operations were conducted in the same manner as Example 20 except for using 0.025 mmol of $FeCl_3$ and 0.05 mmol of triethylamine in place of $NiCl_2$ and N-methylimidazole in Example 20, respectively. The result is shown in Table 3.

Example 33

Under a nitrogen atmosphere, 194.4 mg (1.5 mmol) of dry $NiCl_2$ and 303 mg (3 mmol) of triethylamine were added to 29.99 g of toluene and were stirred at room temperature for 10 minutes. Subsequently, 7.41 g (30.0 mol) of 9,10-dichloroanthracene was added at that temperature and reduced-pressure nitrogen replacement was conducted. To the reaction mixture, 3.8 ml (3.8 mmol) of a 1.0 mol/l solution of methylmagnesium bromide in tetrahydrofuran was added and then stirred at 25° C. for another 10 minutes. To the resulting reaction mixture, 69 ml (69 mmol) of a 1 mol/l solution of phenylmagnesium bromide in tetrahydrofuran was added dropwise over 50 minutes and stirred for 4 hours while being heated under reflux. The resulting mixture was washed once with 54.7 g of a saturated aqueous ammonium chloride solution and twice with 50.4 g of ion exchange water. To the organic layer, 50.4 g of methanol was added dropwise and then cooled to room temperature. Crystals formed were separated by filtration, washed with 30.4 g of in ethanol and dried, resulting in 7.97 g of desired 9,10-diphenylanthracene (yield: 80.4%, purity: 99% or higher). No triethylamine was detected in the crystals. The filtrate contained 12%, in terms of yield, of 9,10-diphenylanthracene.

TABLE 3

| Example | Aryl compound (II) | Grignard reagent (III) | MeMgBr (Reducing agent) | Nickel compound | Nitrogen-containing compound | Solvent | Content of substituted aromatic compound |
|---|---|---|---|---|---|---|---|
| Example 20 | o-Bromotoluene | 2,6-Dimethylphenylmagnesium bromide | Not added | NiCl$_2$ | N-Methylimidazole | THF | 81.7% |
| Example 21 | o-Bromotoluene | 2,6-Dimethylphenylmagnesium bromide | Added | NiCl$_2$ | N-Methylimidazole | THF | 92.8% |
| Example 22 | o-Bromotoluene | 2,6-Dimethylphenylmagnesium bromide | Added | NiCl$_2$ | N,N,N',N'',N''-Pentamethyldiethylenetriamine | THF | 79.1% |
| Example 23 | o-Bromotoluene | 2,6-Dimethylphenylmagnesium bromide | Added | NiCl$_2$ | Tris (2-methoxyethyl-2'-ethoxy)-amine | THF | 81.5% |
| Example 24 | 2-Methyl-1-bromonaphthalene | o-Tolylmagnesium chloride | Not added | NiCl$_2$ | Ttriethylamine | THF | 77.5% |
| Example 25 | 2-Methyl-1-bromonaphthalene | o-Tolylmagnesium chloride | Added | NiCl$_2$ | 1,8-Diazabicyclo-[5.4.0]-undec-7-ene | THF | 84.1% |
| Example 26 | 3-Bromo-o-xylene | o-Tolylmagnesium chloride | Added | NiCl$_2$ | 4-(N,N-dimethylamino)pyridine | THF | 71.7% |
| Example 27 | 9-Bromoanthracene | 2-Naphthylmagnesium bromide | Added | NiCl$_2$ | Triethylamine | THF | 95.1% |
| Example 28 | 9-Chloroanthracene | Phenylmagnesium bromide | Added | NiCl$_2$ | N-Methylimidazole | THF | 92.3% |
| Example 29 | 9,10-Dichloroanthracene | Phenylmagnesium bromide | Added | NiCl$_2$ | Triethylamine | THF | 96.2% |
| Example 30 | o-Chlorotoluene | Phenylmagnesium bromide | Added | NiCl$_2$ | 1,8-Diazabicyclo-[5.4.0]-undec-7-ene | THF | 66.7% |
| Example 31 | m-Bromotoluene | Phenylmagnesium bromide | Added | NiCl$_2$ | Triethylamine | THF | 62.8% |
| Example 32 | 2-Bromobiphenyl | Phenylmagnesium bromide | Added | NiCl$_2$ | Triethylamine | Diglyme | 89.2%* |
| Comparative Example 3 | o-Bromotoluene | 2,6-Dimethylphenylmagnesium bromide | Added | NiCl$_2$ | 2,2'-Bipyridyl | THF | 9.5% |
| Comparative Example 4 | m-Bromotoluene | Phenylmagnesium bromide | Added | NiCl$_2$ | 2,2'-Bipyridyl | THF | 52.3% |
| Comparative Example 5 | 2-Bromobiphenyl | Phenylmagnesium bromide | Added | NiCl$_2$ | 2,2'-Bipyridyl | Diglyme | 8.1%* |
| Comparative Example 6 | o-Bromotoluene | 2,6-Dimethylphenylmagnesium bromide | Not added | FeCl$_3$ | Triethylamine | THF | 0.9% |

*Yield calculated by a GC absolute working curve method using a standard sample

What is claimed is:

1. A method for producing a biaryl compound of formula (I):

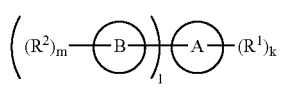
(I)

wherein
R$^1$ is the same or different and independently denotes a substituted or unsubstituted aliphatic hydrocarbon group, a substituted or unsubstituted aryl group, a substituted or unsubstituted alkoxy group, a substituted or unsubstituted aryloxy group, or a, fluorine atom,
A denotes an aromatic hydrocarbon ring having from 6 to 14 carbon atoms or a pyridine ring,
B denotes an aromatic hydrocarbon ring having from 6 to 14 carbon atoms,
k and m independently denote an integer of from 0 to 5, and l denotes an integer of 1 or 2, which method comprises reacting an aromatic compound of formula (II):

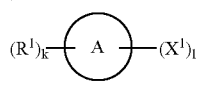
(II)

wherein R$^1$, k and l denote the same as defined above, and X$^1$ denotes a leaving group, with a Grignard reagent of formula (III):

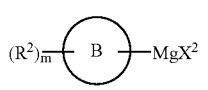
(III)

wherein R$^2$, B, and m denote the same as defined above, and
X$^2$ denote a chlorine, bromine or iodine atom, in the presence of a cyclic ether, or an acyclic ether having two or more ether oxygens in the molecule and a nickel catalyst consisting essentially of a nickel compound and a nitrogen-containing compound, provided that the nitrogen-containing compound is not 2,2'-bipyridyl.

2. A method according to claim 1, wherein the leaving group in formula (I) is a chlorine atom, a bromine atom, an iodine atom, a hydrocarbylsulfonate group, a halogen-substituted hydrocarbyl, group, or a diazonium group.

3. A method according to claim 2, wherein the leaving group is a methanesulfonate group or a p-toluenesulfonate group.

4. A method according to claim 2, wherein the leaving group is a trifluoromethanesulfonate group.

5. A method according to claim 1, wherein the nickel compound is a nickel salt(II) or a nickel complex (0).

6. A method according to claim 5, wherein the nickel compound is nickel halide(II), nickel nitrate(II), nickel acetate(II), nickel acetylacetonate(II), bis(1,5-cyclooctadiene)nickel (0), or nickel carbonyl(0).

7. A method according to claim 1, wherein $R^1$ and $R^2$ independently represent a straight chain or branched chain, saturated or unsaturated aliphatic hydrocarbon group having from 1 to 12 carbon atoms, a straight chain or branched, cyclic or acyclic alkoxy group having from 1 to 12 carbon atoms, an aryl group having from 6 to 14 carbon atoms, or an aryloxy group having from 6 to 14 carbon atoms, all of which may be substituted with at least one substituent group selected from a straight chain, branched, or cyclic, saturated or unsaturated aliphatic hydrocarbon group having from 1 to 12 carbon atoms, an aryl group having from 6 to 14 carbon atoms, a straight chain or branched, cyclic alkoxy group having from 1 to 12 carbon atoms, and an aryloxy group having from 6 to 14 carbon atoms.

8. A method according to claim 1, wherein the nitrogen-containing compound is an alkylamine having from 1 to 3 nitrogen atoms and from 4- to 20 carbon atoms, an alkoxyalkylamine having from 1 to 2 nitrogen atoms, from 5 to 20 carbon atoms and from 1 to 6 oxygen atoms, N-alkylguanidines, N,N-dialkylpiperazine, alkylpiperidine, N-alkylpyrrolidine, N,N',N"-trialkyltxiazine, N-alkylmorpholine, bicycloalkylamine, enamine, diazabicycloalkene, pyridine, N,N-dialkylaminopyridine, and alkylpyridine pyrrole and alkylpyrrole, imidazole which may be substituted with an alkyl group having from 1 to 15 carbon atoms, aryl-alkyl group or an aryl group, group, pyrazole which may be substituted with an alkyl or aryl triazole which may be substituted with an alkyl group, tetrazole which may be substituted with an alkyl group, benzimidazole which maybe substituted with an alkyl group, benzotriazole which maybe substituted with an alkyl group, oxazole which may be substituted with an alkyl group, benzoxazole compound, benzothiazole compound, carbazole and N-alkylcarbazole, quinoline compound phthalazine compound, quinazoline compound, pyrimidine which may be substituted with an alkyl group, piperazine, piperidine, pyrrolidine, N,N',N""-trialkyltriazacycloalkane, morpholine, or a cyclic urea compound.

9. A method according to claim 1, wherein the nitrogen-containing compound is acycl.ic nitrogen-containing compound or cyclic nitrogen-containing compounds, wherein the nitrogen atom or atoms of the acyclic nitrogen-containing compound and cyclic nitrogen-containing compounds are tertiary nitrogen atom or atoms.

10. A method according to claim 9, wherein the nitrogen-containing compound is triethylamine, diisopropylethylamine, N,N,N',N'-tetramethylethylene-1,2-diamine, N,N, N',N'-tetramethylpropylene-1,3-diamine, N, N, N', N", N"-pentamethyldiethylenetriamine, tris(2-(2-methoxyethoxy)ethyl) amine, tris(2-methoxyethyl)amine, N,N-diethyl-2-methoxyethylamine, tetramethylguanidine, 1,4-dimethylpiperazine, N-methylpiperidine, 1,2,2,6,6-pentamethylpiperidine, N-ethylpyrrolidine, 1,3,5-trimethyltriazine, 1,4,7-trimethyltriazacyclononane, N'-methylmorpholine, 1,4-diazabicyclo[2.2.2.]octane, quinuclidine, N-( 1-cyclopentenyl)morpholine, 1,8-diazabicyclo-[5.4.0]-undec-7-ene, 1,5-diazabicyclo-[4.3.0]-non-5-ene, N,N-dimethylaminopyridine, N-isopropylpyrrole, N-phenylimidazole, N-methylimidazole, 1,5-dimethylimidazole, N+-benzylimidazole, 1-phenyl-1,2-pyrazole, 1-methyl-1,2-pyrazole, 1-methyl-1,2,3-triazole, 1,5-dicyclohexyl-1,2,3,4-tetrazole, 1-methylbenzimidazole, 1-methyl-1,2,3-benzotriazole, 2,4,5-trimethyloxazole, benzoxazole, benzothiazole, N-ethylcarbazole, quinoline, phthalazine, quinazoline, 4,-ethylpyrimidine, N,N-dimethylimidazolidone or N,N-dimethyl-propyleneurea.

11. A method according to any one of claims 1 to 4, wherein the cyclic ether is 1,4-dioxane.

12. A method according to any one of claims 1 to 4, wherein the chain ether having two or more ether oxygens in the molecule is a glyme.

13. A method according to claim 8, wherein the nitrogen-containing compound is the imidazole which may be substituted with an alkyl group, aryl-alkyl group or an aryl group, the diazabicycloalkene, the N,N-dialkylazninopyridine, the alkoxyalkylamine, or the alkylamine.

14. A method according to claim 8, wherein the nitrogen-containing compound is N-methylimidazole.

15. A method according to claim 8, wherein the nitrogen-containing compound is 1,8-diazabicyclo-[5.4.0]-undec-7-ene.

16. A method according to any one of claims 2 to 7, wherein at least one ortho-carbon atom of the aromatic compound of formula (II) or the Grignard compound of formula (III) is substituted with a hydrogen atom, wherein the ortho-carbon atom is defined in relation to the carbon atom bonded with $X^1$ group or $MgX^2$ group.

17. A method according to claim 8, wherein the aromatic compound of formula (II) is a compound of formula (IV):

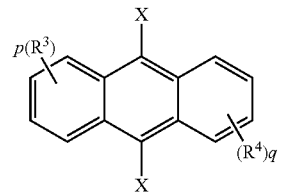

wherein $R^3$ and $R^4$ are the same or different and independently denote an aliphatic hydrocarbon group, an aryl group, an alkoxyl group, an aryloxy group, an aralkyloxy group or a fluorine atom, p and q independently denote an integer of from 0 to 4, and p+q<5.

18. A method according to claim 11, wherein the nitrogen-containing compound is triethylamine.

19. A method according to any one of claims 1 to 9, wherein the reaction is conducted at a temperature range of from not lower than −40° C. to not higher than 200° C.

* * * * *